(12) United States Patent
Duffield et al.

(10) Patent No.: US 11,684,490 B2
(45) Date of Patent: Jun. 27, 2023

(54) INTERBODY FUSION DEVICE AND SYSTEM FOR IMPLANTATION

(71) Applicant: Institute for Musculoskeletal Science and Education, Ltd., King of Prussia, PA (US)

(72) Inventors: William Duffield, Collegeville, PA (US); Katherine Elizabeth Brown, Garnet Valley, PA (US); James A. Sack, Elverson, PA (US)

(73) Assignee: Institute for Musculoskeletal Science and Education, Ltd., King of Prussia, PA (US)

( * ) Notice: Subject to any disclaimer, the term of this patent is extended or adjusted under 35 U.S.C. 154(b) by 561 days.

(21) Appl. No.: 16/735,384

(22) Filed: Jan. 6, 2020

(65) Prior Publication Data
US 2020/0253746 A1    Aug. 13, 2020

Related U.S. Application Data

(63) Continuation of application No. 15/885,230, filed on Jan. 31, 2018, now Pat. No. 10,524,930, which is a continuation of application No. 15/623,463, filed on Jun. 15, 2017, now Pat. No. 9,949,846, which is a continuation of application No. 15/194,323, filed on Jun. 27, 2016, now Pat. No. 9,707,100.

(60) Provisional application No. 62/236,698, filed on Oct. 2, 2015, provisional application No. 62/210,707, filed on Aug. 27, 2015, provisional application No. 62/184,638, filed on Jun. 25, 2015.

(51) Int. Cl.
*A61F 2/44* (2006.01)
*A61F 2/46* (2006.01)
*A61F 2/30* (2006.01)

(52) U.S. Cl.
CPC ............ *A61F 2/4611* (2013.01); *A61F 2/447* (2013.01); *A61F 2/4455* (2013.01); *A61F 2002/30579* (2013.01); *A61F 2002/30593* (2013.01); *A61F 2220/0008* (2013.01)

(58) Field of Classification Search
CPC .. A61F 2002/30579; A61F 2002/30593; A61F 2002/4475; A61F 2/4611; A61F 2/4455; A61F 2/447; A61F 2220/0008
USPC .................... 623/17.11, 17.16; 606/246–249
See application file for complete search history.

(56) References Cited

U.S. PATENT DOCUMENTS

| | | | | |
|---|---|---|---|---|
| 6,113,638 A | * | 9/2000 | Williams | A61F 2/4455 606/279 |
| 6,527,803 B1 | * | 3/2003 | Crozet | A61F 2/442 606/31 |

(Continued)

*Primary Examiner* — Eduardo C Robert
*Assistant Examiner* — David C Comstock
(74) *Attorney, Agent, or Firm* — Plumsea Law Group, LLC

(57) ABSTRACT

An implant includes a body and a bone fixation system. The body includes an interior area disposed between a superior surface and an opposite inferior surface spaced from the superior surface in a vertical direction. In addition, the bone fixation system includes at least one blade disposed within the interior area of the body in an insertion position. Also, the bone fixation system further includes at least one strike plate engaging the at least one blade in the interior area of the body, the at least one strike plate being configured to move the at least one blade from the insertion position to an impaction position in which at least a portion of the blade protrudes past one of the superior surface and inferior surface of the body.

19 Claims, 21 Drawing Sheets

(56) References Cited

U.S. PATENT DOCUMENTS

| | | | | |
|---|---|---|---|---|
| 8,398,713 | B2* | 3/2013 | Weiman | A61F 2/44 |
| | | | | 623/17.11 |
| 10,524,930 | B2* | 1/2020 | Duffield | A61F 2/4455 |
| 2010/0185289 | A1* | 7/2010 | Kirwan | A61F 2/447 |
| | | | | 623/17.11 |
| 2011/0319997 | A1* | 12/2011 | Glerum | A61F 2/442 |
| | | | | 623/17.11 |
| 2013/0110242 | A1* | 5/2013 | Kirwan | A61F 2/447 |
| | | | | 623/17.16 |
| 2014/0074241 | A1* | 3/2014 | McConnell | A61F 2/447 |
| | | | | 623/17.16 |

* cited by examiner

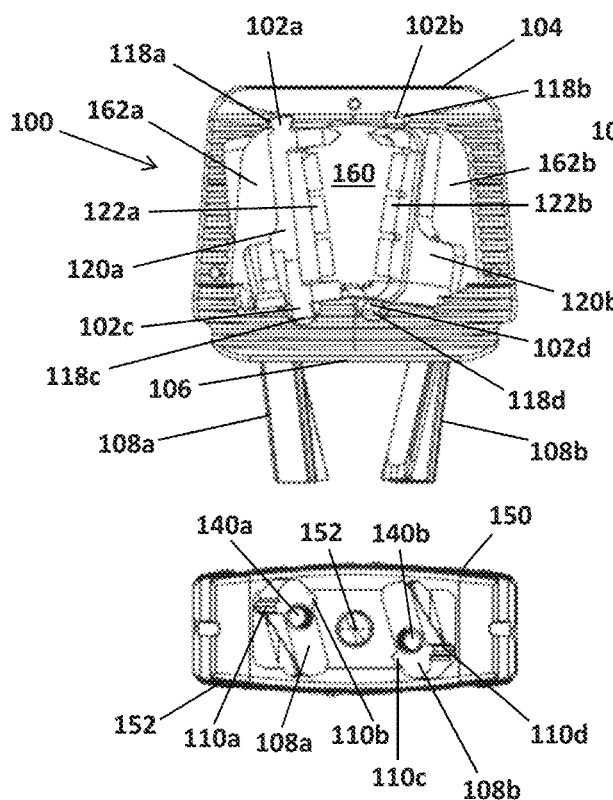
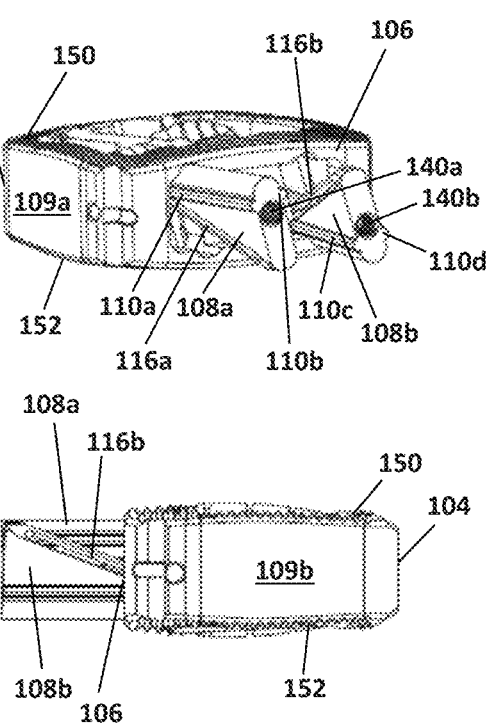
FIG. 1A
FIG. 1B
FIG. 1C
FIG. 1D

FIG. 2A
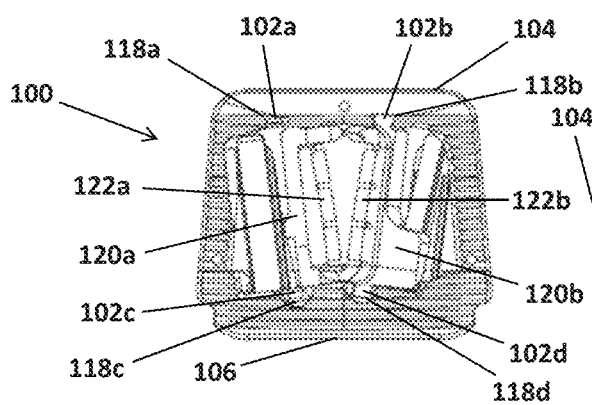
FIG. 2B
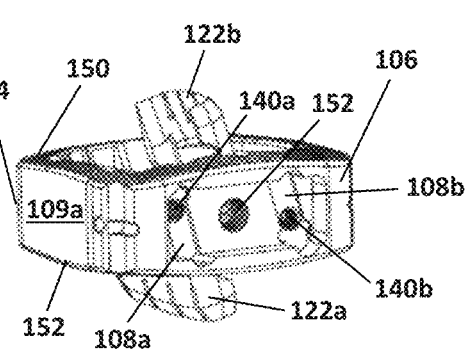
FIG. 2C
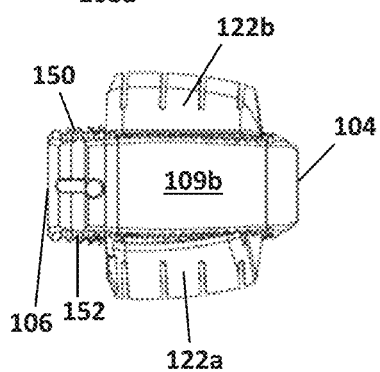
FIG. 2D

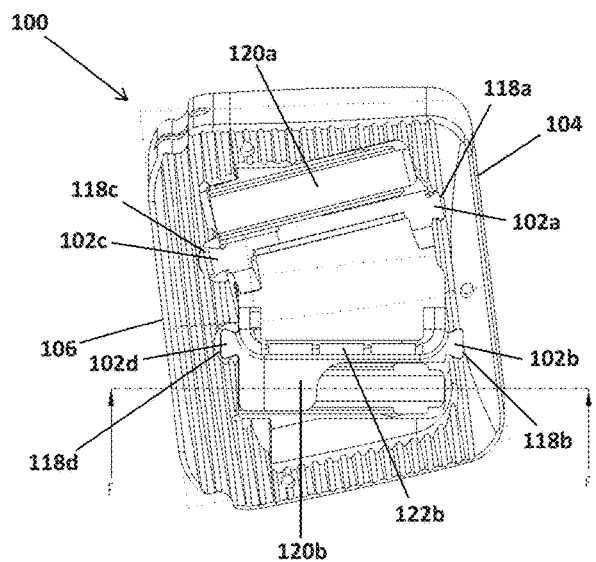
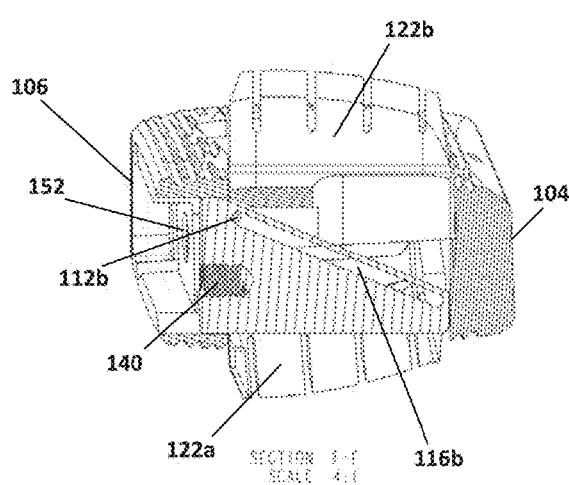
FIG. 4A
FIG. 4B

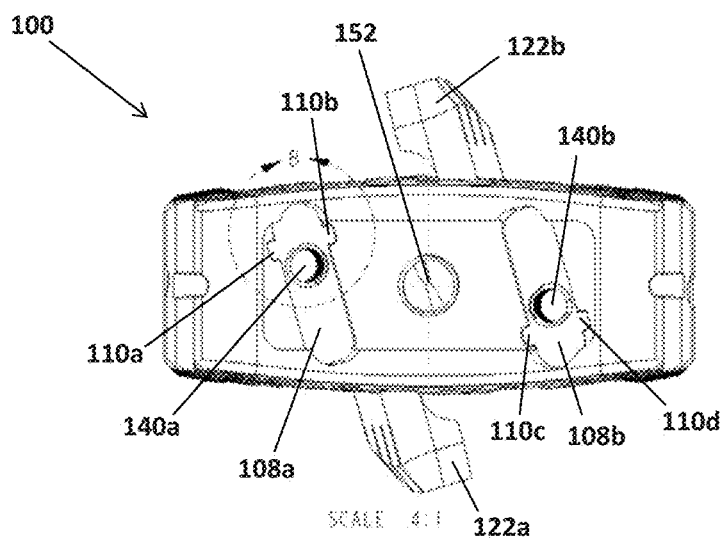
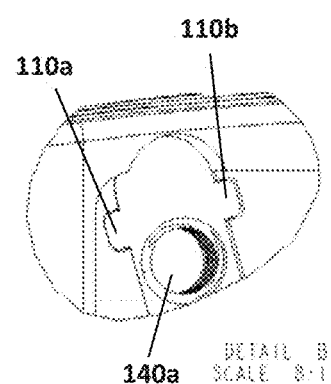
FIG. 7A
FIG. 7B

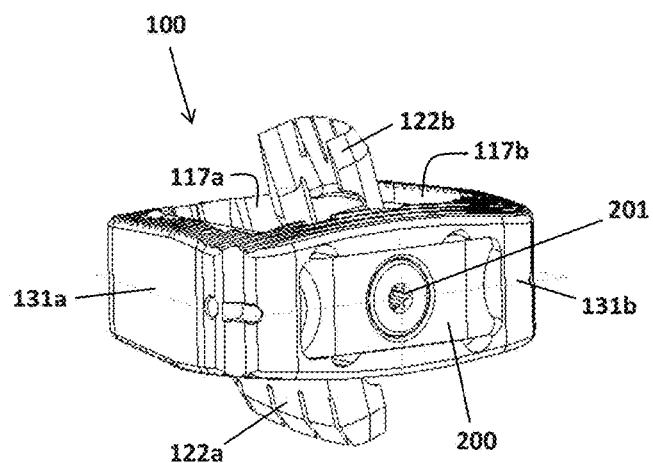 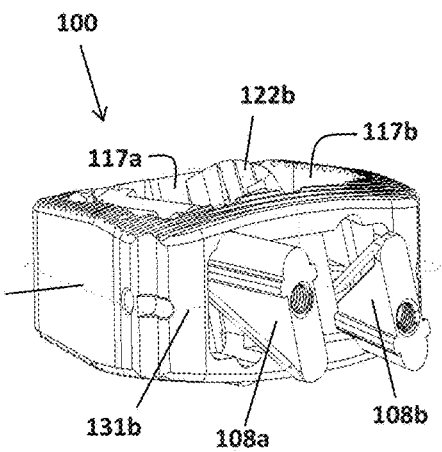
FIG. 10A
FIG. 10B

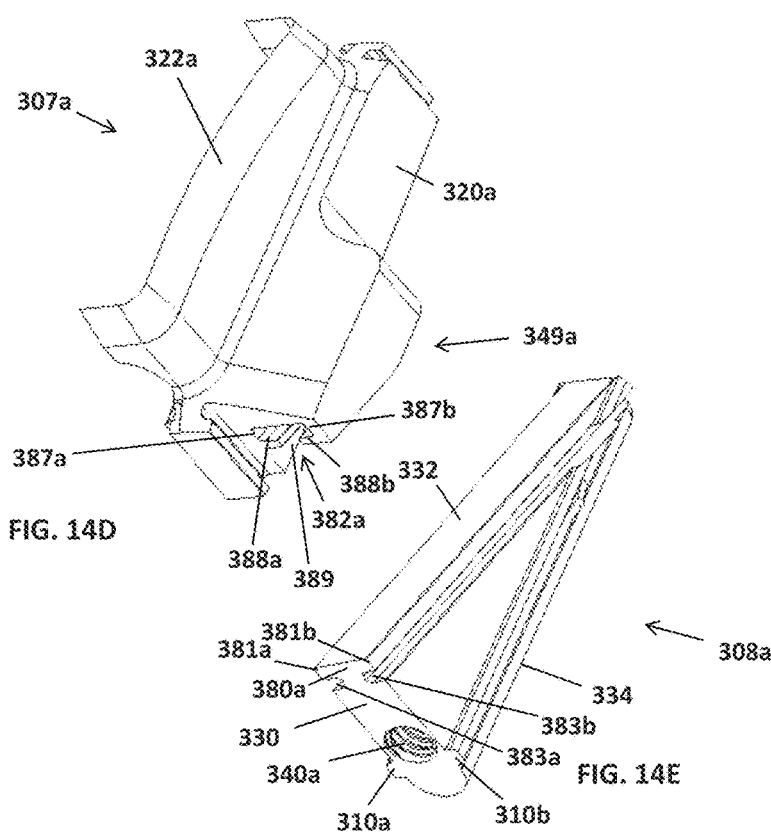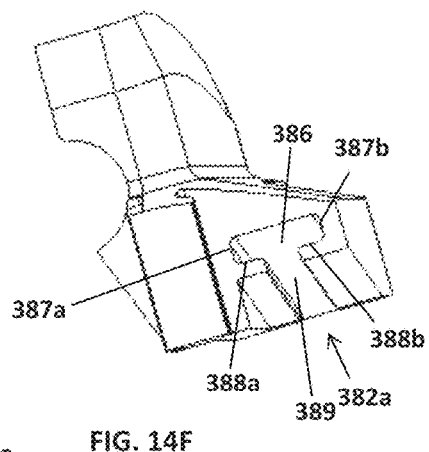

INTERBODY FUSION DEVICE AND SYSTEM FOR IMPLANTATION

CROSS-REFERENCE TO RELATED APPLICATION(S)

This application is a continuation of co-pending Duffield et al., U.S. Application Publ. No. 2019/0038433, published on Feb. 7, 2019, which is a continuation of Duffield et al., U.S. Application Publ. No. 2017/0281434, published on Oct. 5, 2017, which is a continuation of U.S. Pat. No. 9,707,100, issued on Jul. 18, 2017, all of which are entitled "Interbody Fusion Device and System for Implantation," and all of which claim priority to U.S. Provisional Application Ser. No. 62/184,638, filed on Jun. 25, 2015; U.S. Provisional Application Ser. No. 62/210,707, filed on Aug. 27, 2015; and U.S. Provisional Application Ser. No. 62/236,698, filed on Oct. 2, 2015. The disclosures of all of the patent documents listed above are incorporated herein by reference in their entirety.

FIELD OF THE INVENTION

The present invention relates generally to interbody fusion implants and methods, and systems for fixing such implants in place.

BACKGROUND OF THE INVENTION

Anterior lumbar interbody fusion (ALIF) is a type of spinal fusion that utilizes an anterior (front—through the abdominal region) approach to fuse the lumbar spine bones together. The intervertebral disc is removed and replaced with a bone (or metal) spacer. The anterior technique is often used when multiple spinal levels are being fused and multiple discs need to be removed. ALIF may be performed in conjunction with or without a posterior decompression (laminectomy) and/or instrumentation (use of metal screws/rods). The anterior approach is also used when only one spinal level is fused and a posterior decompression and/or instrumentation are not required. Although the anterior lumbar approach involves retracting (moving out of the way, temporarily) large blood vessels (e.g., aorta, vena cava) and the intestines, there is a wide exposure of the intervertebral disc without retraction of the spinal nerves and neurologic structures (and therefore, a decreased risk of neurologic injury).

ALIF is commonly performed for a variety of painful spinal conditions, such as spondylolisthesis and degenerative disc disease.

The ALIF approach is advantageous in that, unlike the posterior lumbar interbody fusion (PLIF) and posterolateral gutter approaches, both the back muscles and nerves remain undisturbed.

Another advantage with the ALIF approach is that placing the bone graft in the front of the spine places it in compression, and bone in compression tends to fuse better.

Additionally, a much larger implant can be inserted through an anterior approach, and this provides for better initial stability of the fusion construct.

However, the ALIF procedure also involves resection of the anterior longitudinal ligament, which can destabilize the implant.

Therefore, surgeons often combine ALIF with a posterior approach (anterior/posterior fusions) because of the need to provide more rigid fixation than an anterior approach alone currently provides. Additionally, stabilization and fixation devices have been added to a standard interbody fusion spacer to stabilize and fix the spacer in place.

The lateral approach provides an alternate route to the spine that disturbs fewer structures and tissues. This, in combination with small incisions, means less discomfort for the patient and fewer risks of complications. With a lateral lumbar interbody fusion (lateral LIF), the surgeon approaches the back through a small incision in the side of the body, using special tools and techniques. A lateral LIF is also commonly referred to as DLIF® (Direct Lateral Interbody Fusion), XLIF® (eXtreme Lateral Interbody Fusion), and transposas interbody fusion.

Typically, patients who are candidates for this surgery are those who would have needed an incision in the abdomen in order for the surgeon to reach the area of concern. Approaching the spine through the abdomen means the surgeon must bypass large blood vessels, nerves, muscles, and organs that are in the way. This can prolong recovery following surgery and, in rare cases, cause complications such as nerve or blood vessel damage.

Many existing interbody fusion spacer systems require multiple actions on the part of the surgeon with respect to implant insertion, and fixation of the implant to the vertebral bodies.

For example, the INDEPENDENCE® Spacer System (Globus Medical, Inc.) integrates a stabilization plate and a PEEK interbody spacer into a preassembled system. INDEPENDENCE® also incorporates a smooth screw blocking mechanism, minimizing disruption to the anatomy surrounding the surgical site and may lessen the long term impact from surgery. However, this system requires multiple actions by a surgeon to insert and fix the system in place.

Additionally the use of a screw fixation system has a number of disadvantages. Screw fixation systems can require the use of awls, drills, and/or taps to prepare a hole in the vertebrae. Some screw systems require the use of screwdrivers having different lengths to insert the screw or an initial driver to insert the screw most of the way into the vertebrae and then a torque driver to execute the final tightening.

Screw fixation devices require a specific angle of insertion that requires a larger soft tissue exposure/corridor than necessary to insert the implant itself. Sometimes these angles require undue pressure on the surrounding soft tissues which could place abdominal viscera and blood vessels at risk. These fixed angles required to insert the screws can limit the ability to insert the fixation devices at the L5-S1 disc, where the symphysis pubis may inhibit access.

Additionally, the fixed angles for screw insertion and limited soft tissue exposure can place excess pressure on the insertion tool and cause the screw to be inserted inappropriately and possibly strip the screw at the bone-screw interface or the screw-anterior plate interface.

While overcoming some of the limitations associated with fixed-angle screw insertion some vertebral fixation systems utilize variable angle screw insertion, however these systems may not provide rigid fixation to the plate/implant and vertebrae.

Screw systems, fixed or variable angle, provide little surface area contact within the vertebra to adequately resist the forces of flexion, extension, rotation, and translation/shear. A fixation system that effectively neutralizes these forces is necessary for rigid fixation. Rigid fixation eliminates the need for supplemental external immobilization devices (braces) and allows early patient mobilization and return to more normal activity.

Instrumentation and specialized tools for insertion of an intervertebral implant is yet another design parameter to consider when designing a spacer. Spinal fusion procedures can present several challenges because of the small clearances around the spacer when it is being inserted into the desired position. For instance, the instrumentation used may securely grip the implant on opposing sides or surfaces. In U.S. Pat. No. 6,520,993 to James, et al., for example, the superior and inferior surfaces have one or more regions in which no gripping teeth are present. These protrusion-free zones enable the implant to be grasped and manipulated by elongate rectangular blades. However, the clearance required to insert the spacer must be higher than the spacer itself to accommodate the required instrumentation. For this reason, distraction of the treated area typically is greater than the size of the implant itself.

Similarly, with the gripping tools used to manipulate and insert the implant on the sides of the spacer, additional clearance typically is needed to accommodate the added width of the insertion tool blades. Such increases in height or width of the profile of the spacer, when in communication with instrumentation, require additional space in order to insert the spacer. In some circumstances, this requires increasing the size of the distracted area in the patient. Further, sometimes creating this additional space can be difficult.

There remains a need for improved fixation devices for use in interbody fusions, such as ALIF and lateral LIF.

Therefore it is an object of the invention to provide improved intervertebral implants and kits.

It is a further object of the invention to provide improved methods for achieving intervertebral fusions in the lumbar or cervical spine.

It is yet a further object of the invention to provide an implant that can be removed without destroying the implant.

SUMMARY OF THE INVENTION

Intervertebral implants, kits and methods for an anterior lumbar interbody fusion (ALIF) or a lateral lumbar interbody fusion (lateral LIF) are described herein. The intervertebral implant is a multi-component fusion device. The implant contains an implant body with a fixation system incorporated therein. The fixation system includes two deployable blades and one or more strike plates that are able to push the blades from a first insertion position to a second, impaction position.

The blades contain a blade region and a support region and are positioned inside the implant such that one blade is able to move superiorly and the other blade is able to move inferiorly when deployed. Typically, the support region has an outer surface, an inner surface and two ends, each of which contains a protrusion. Each protrusion fits in a unidirectional/axial track located on an interior surface of the implant body and allow for linear translation of the blade relative to the implant body. The protrusions on the ends of the support region of the blades fit inside and in sliding relation to the tracks, allowing the blades to slide in a general vertical motion or at a compound angle inside the implant. In some embodiments the protrusion is in the shape of a dovetail (referred to herein as "dovetail" or "dovetail protrusion"), and the tracks are correspondingly shaped dovetail tracks.

In a preferred embodiment, the implant also contains two strike plates that are in the shape of a right-angled wedge. The hypotenuse surface of each wedge fits into a track containing an angled ramp located on the support regions of the blades, allowing the strike plates to slide along the track from a first, insertion position to a second, impaction position. In some embodiments, the hypotenuse surface of each wedge is the upper surface of a protrusion (referred to herein as a "strike plate protrusion") that fits into and slides along a correspondingly shaped track in the support region of the blade. In certain embodiments track is in the shape of a T-shaped track that has an upper surface, two side surfaces, two lower surfaces, and a channel, configured to engage a correspondingly shaped and sized, T-shaped strike plate protrusion on the strike plate.

In the insertion position, the strike plates protrude from one side of the implant and the blades are contained inside the implant. Impaction of the strike plates into the implant causes them to slide along the ramps, pushing one blade superiorly and the other blade inferiorly along the tracks on the interior surfaces of the implant. In the resulting impaction position, the blade regions of the blades are pushed out of the implant, protrude past the superior and inferior surfaces of the implant and engage the superior and inferior vertebral bodies.

Following insertion of the implant into the spine and impaction of the blades, a front cover plate may be affixed to the surface of the implant through which the strike plates protrude when in the insertion position to prevent the strike plates from backing out.

If needed, the front cover plate can be removed and the blades can be retracted to allow for removal of the implant.

BRIEF DESCRIPTION OF THE DRAWINGS

FIGS. 1A-1D show various views of an exemplary implant in its insertion position, with the strike plates protruding from the anterior side of the implant and the blades inside the implant. FIGS. 1A, 1B, 1C, and 1D respectively show plan, perspective, elevation, and side views of the implant.

FIGS. 2A-2D show various views of the implant depicted in FIGS. 1A-1D in its impaction position. With the strike plates impacted, the two blades are forced superiorly and inferiorly, respectively. FIGS. 2A, 2B, 2C, and 2D respectively show plan, perspective, elevation, and side views of the implant.

FIGS. 4A and 4B show perspective and cross-sectional perspective views (respectively) of the implant depicted in FIGS. 1A-1D in the impaction position.

FIG. 4B is a cross-sectional view of FIG. 4A taken at section F-F.

FIG. 5B is a cross-sectional view of FIG. 5A taken at section F-F.

FIGS. 7A and 7B show an elevation view (FIG. 7A) of the implant depicted in FIGS. 1A-1D in the impaction position with a magnified partial view (FIG. 7B) showing retention rails (110a-110d) on either side of the strike plates (108a and 108b).

FIGS. 10A and 10B show perspective views of the implant depicted in FIGS. 1A-1D in the impaction and insertion positions. FIG. 10A shows a perspective view of the implant in its final impaction position with a cover plate attached to the anterior side of the implant. FIG. 10B shows a perspective view of the implant in the insertion position.

FIG. 13A shows a perspective view with the blade portion facing up. FIG. 13B shows a perspective view with the blade portion facing down and the angled ramp facing up.

FIG. 13C shows another perspective view with the blade portion facing down and showing the interior surface of the blade. FIG. 13D shows another perspective view with the blade portion facing up and the support portion visible, which shows the outer surfaces of the blade. FIG. 13E shows a side view of a blade. FIG. 13F shows a cross sectional side view of a blade showing the angle between the ramp and plane (P). FIG. 13G shows a cross sectional perspective view of a blade showing the ramp on the support region of the blade.

FIG. 14A shows an elevation view with the strike plate in the impaction position. FIG. 14B shows a perspective view with the strike plate in the insertion position. FIG. 14C shows a side view, with the strike plate in the insertion position. FIGS. 14D and 14E show perspective views of a blade and a strike plate, respectively, where the support region of the blade has a T-shaped track to accommodate a T-shaped protrusion on the respective strike plate. FIG. 14F shows another perspective view of the blade depicted in FIG. 14D.

DETAILED DESCRIPTION

I. Definitions

Figure 3:
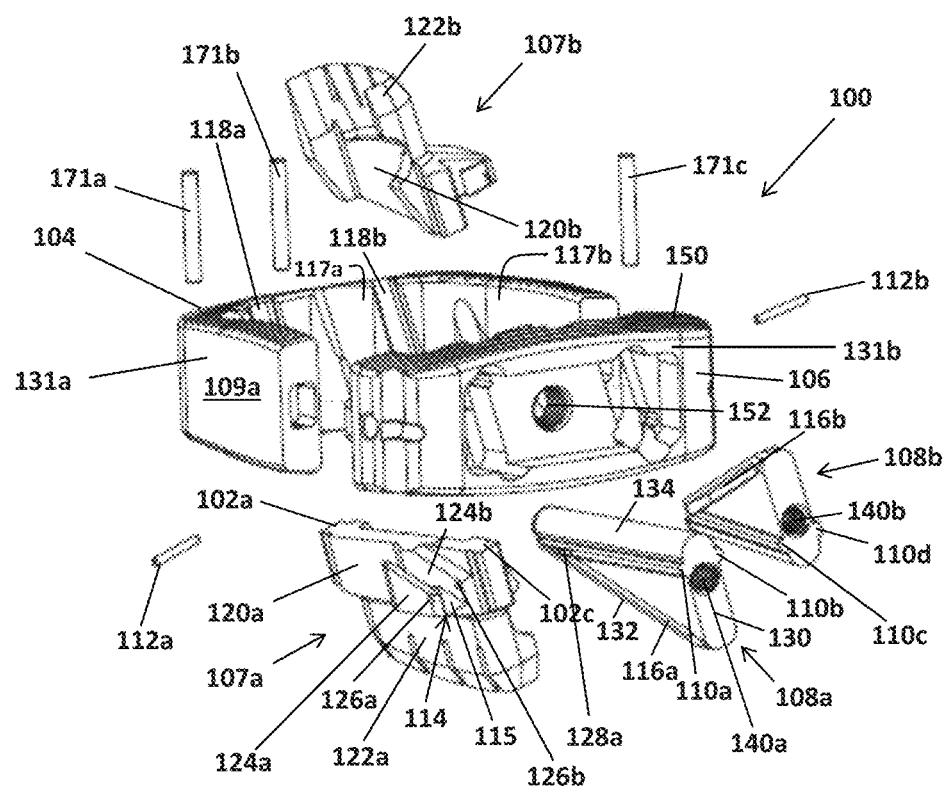
FIG. 3 shows an exploded view of the implant depicted in FIGS. 1A-1D.

As used herein, the term "compound angle" refers to the resultant of two component angles where each component angle exists in a different plane. For example, component angle A1 and component angle A2 in FIGS. 12A and 12B lie in different planes. The resultant compound angle is defined by both of the component angles.

As used herein, the term "right-angled wedge" refers to a wedge that is shaped like a right-angled triangle when viewed from the side.

As used herein, the term "hypotenuse surface" refers to the outer surface of the longest side of a right-angled wedge in the strike plate, which is opposite the right angle.

As used herein, the term "impaction position" refers to the position in which the one or more strike plates are pushed into the implant, and the blade region of the blades protrudes past the superior and inferior surfaces of the implant.

As used herein, the term "insertion position" refers to the position in which the one or more strike plates protrude from one side of the implant body. In this position, the blades (i.e. both the support region and the blade region) are located and contained inside the implant.

As used herein, the term "retention bump" refers to a protrusion on a strike plate that keeps the blades in the insertion position until they are deployed.

II. Implant

A. Body

The intervertebral implants have a three dimensional body suitable for insertion between vertebrae.

The body is defined by two lateral side walls, an anterior side, a posterior side, a superior surface and an inferior surface. The body contains four interior surfaces ($117a$, $117b$, etc.) corresponding with the lateral side walls, the anterior side and the posterior side, and six exterior surfaces ($131a$, $131b$, etc.) corresponding with the lateral side walls, the anterior side, the posterior side, and the superior and inferior surfaces. The implant contains one or more openings, depending on the orientation of the blades and the number of strike plates, such as two or three openings, adjacent to and between the blades, which allow for the insertion of bone graft material. The implant allows the bone to grow through the implant and into the adjacent vertebral bodies. The openings define the void volume in the implant. The percent (%) void volume in each implant depends on the size, shape and type of implant. For example, the void volume in an implant, such as one used in an interbody fusion, can range from about 20% to about 60%. For ALIF implants, the % void volume ranges from 20% to 50%. Typically for lateral LIF implants the implants have a greater void volume compared to ALIF implants of a similar height. For example, for some lateral LIF implants, the % void volume ranges from 30% to 60%.

The implants and fixation systems may contain one or more threaded holes, slots or channels to mate with instruments to facilitate holding and inserting the implants. For example, the one or more strike plates may contain threaded connections or holes ($140a$, $140b$, $340a$, $340b$) on their end(s) that connect to an insertion tool for insertion of the implant into or removal of the implant from the vertebral body.

The implant can be formed from any suitable biocompatible, non-degradable material with sufficient strength. Typical materials include titanium and inert, biocompatible polymers, such as polyether ether ketone (PEEK) (e.g. PEEK-OPTIMA®, Invibio Inc.). Optionally, the implant contains a radiopaque marker to facilitate visualization during imaging.

One embodiment of an exemplary implant (100) suitable for insertion into a patient using an anterior approach is illustrated in FIGS. 1A-9B. As shown in FIG. 1A, the implant body is adapted for insertion within an intervertebral space between adjacent vertebral bodies and includes a first insertion side (posterior side) (104), a second side (anterior side) (106) opposite the first insertion side, a first lateral side portion (109a), a second lateral side portion (109b), a superior surface (150) and an inferior surface (152). In a preferred embodiment, the implant has a trapezoidal shape, with the posterior side being the shorter of the two parallel sides. One of ordinary skill in the art will appreciate that implants having other shapes may be used, with the particular shape of the implant selected for the particular insertion method and site.

The superior and inferior surfaces of the implant, which contact the superior vertebral body and the inferior vertebral body, respectively, typically contain teeth, knurling, ridges or similar projections, to aid in securing the implant to the vertebral endplate and preventing or reducing any shifting of the implant. This also provides initial stability of the implant between the two vertebral bodies following insertion into the intervertebral space.

The implants may be sized and configured for anterior, posterior or lateral approaches and insertion in the lumbar or cervical regions of the spine. In some embodiments the size of the implant body is 23 mm×28 mm. In some embodiments, the size of the implant body is 26 mm×32 mm. In other embodiments, the size of the implant body is 32 mm×38 mm. The lordosis, or angle generated by tangent lines to the curved surfaces of adjacent vertebral endplates, can range from 0° to 30°, optionally from 0° to 10°, 5° to 10°, or 10° to 20°. For example, in some embodiments, the lordosis of the implant is 8°. In other embodiments, the lordosis is 15°. In some embodiments, the implant is 11 mm, 13 mm, 15 mm, 17 mm, 19 mm, or 21 mm tall when measured from the highest and lowest points on the superior and inferior surfaces respectively of either the implant body or the cover plate.

The particular surface shape and curvature, or taper in the anterior-posterior direction as well as between the lateral side surfaces depends upon the location at which the implant is intended to be inserted. For example, the anterior-to-posterior dimension (sagittal plane) of the Lateral LIF implant is less than the anterior-to-posterior dimension of the ALIF implant to allow insertion from a lateral approach. Typical anterior-to-posterior dimensions for a Lateral LIF implant range from about 18 to 26 mm, while for the ALIF, typical anterior-to-posterior dimensions range from about 23 to 32 mm. The left to right dimension of the lateral LIF implant is typically longer than the left to right dimension in an ALIF implant so that it can span the entire width of the vertebral body. The shape of the perimeter of the implant body can be modified for lumbar applications, or for other areas, such as in the cervical area of the spine. In some embodiments, the width (w) of the implant ranges from 28 mm to 38 mm. In a preferred embodiment, the width (w) is 28 mm. In some embodiments, the depth (d) of the implant ranges from 23 mm to 32 mm. In a preferred embodiment, the depth (d) is 23 mm. The height of ALIF and Lateral LIF implants generally ranges from 7 mm to 21 mm. In some preferred embodiments, the height (h) of the implant is 9 mm, 11 mm, 13 mm, or 15 mm. For the lateral LIF, the height typically ranges from 8 mm to 21 mm.

1. Tracks on an Interior Surface of the Implant Body

Figure 6A:
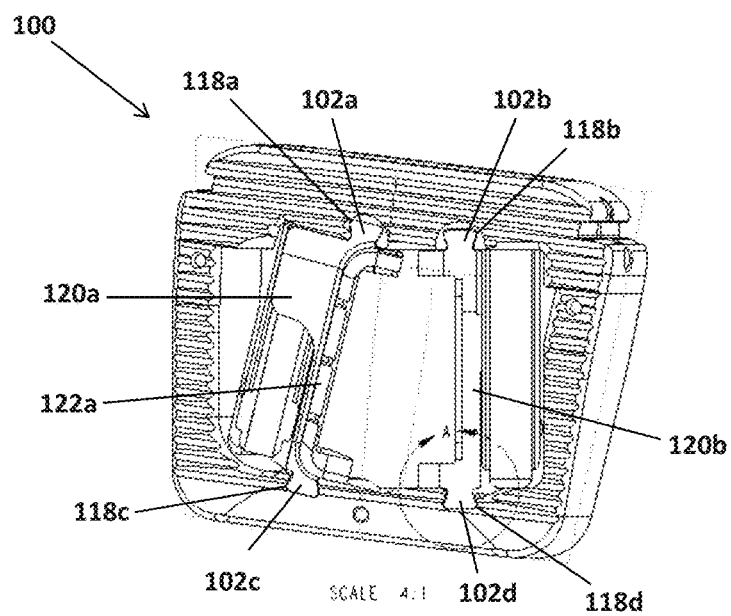
FIGS. 6A and 6B show a perspective view of the implant depicted in FIGS. 1A-1D (FIG. 6A) and a magnified partial view (FIG. 6B) showing a dovetail wedge (102b) protruding from the blade (107b).
Figure 6B:
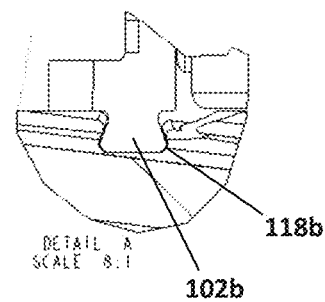
Figure 8A:
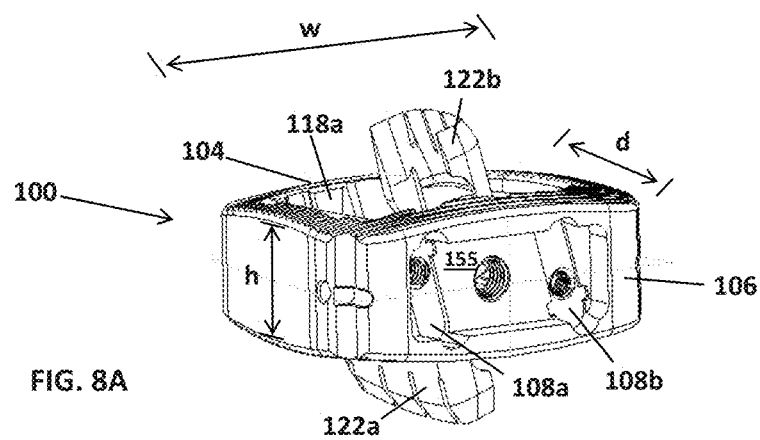
FIGS. 8A and 8B show perspective views of exemplary implants of different sizes.
Figure 8B:
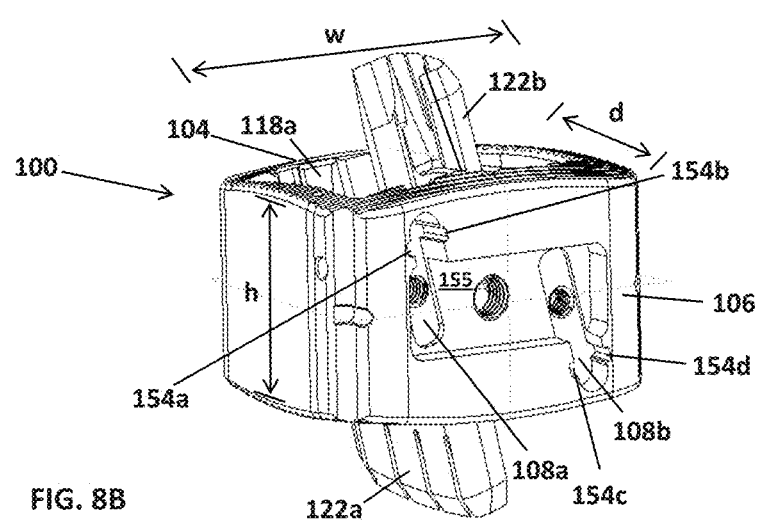

In a preferred embodiment, the implant contains four substantially vertical tracks on two of its interior surfaces, where the interior surfaces are opposite each other. For an ALIF, two of the tracks may be on the interior surface of the posterior side (118a, 118b), and two on the interior surface of the anterior side (118c, 118d). Preferably in the tracks have cross sections in the shape of dovetails (FIGS. 6A and 6B). The dovetail protrusions (102a-102d) located on both ends of the support regions of the two blades are located inside the dovetail tracks. The dovetail tracks allow the blades to slide inside the implant from the first insertion position to the second, impaction position.

One skilled in the art would understand that the track for sliding blades can adopt many different shapes as long as the tracks are complementary in shape to the protrusions on the ends of the support region for each blade. The cross-sectional shape may be a symmetric shape or a non-symmetric shape. Exemplary cross-sectional shapes include but are not limited to T-shapes, C-shapes, I-shapes, dovetailed shapes with angled sides, any portion of a circle, a triangle, an ellipse, a polygon, a star, a square, a rectangle, an oval, a hexagon, or an octagon.

In a preferred embodiment, the implant may contain one or more exterior surfaces, one or more depressions and or one or more screw holes that can be used to facilitate insertion of the implant and/or fixation of a cover plate to the exterior surface of the implant, such as to prevent the strike plates from moving after insertion of the implant between the vertebral bodies. For example, in a preferred embodiment useful for an ALIF, the implant may contain a screw hole (152) or other feature on the exterior surface (131b) of its anterior side (106), allowing the practitioner to attach an insertion tool to the insertion end of the implant and, optionally, to fix a cover plate over the anterior side after insertion of the implant between the vertebral bodies. In other embodiments, such as a LIF, the implant may contain on a lateral side or other side that is used for insertion a screw hole or other feature to facilitate insertion of the implant and, optionally to allow a practitioner to fix a cover plate over that side after insertion of the implant.

The implant can be implanted in the desired location in a patient using known surgical instruments. The number and position of access through-holes, e.g. two, three, four or the like, is dictated by the particular patient's anatomy or other surgical considerations, and is also not intended to be limited by the type of attachment mechanism between the implant and instrumentation.

The implant can be used for anterior, posterior or lateral approaches. The implants can be single-use devices. In some embodiments, the entire implant (including the fixation systems) can be removed from the patient and then later re-inserted.

B. Fixation Systems

The fixation systems described herein are integral with and can move from a first position (the "insertion position"), which allows the implant to maintain a low profile at the time of insertion, to a second position (the "impaction position"), in which the blades are deployed into the proximal superior and inferior vertebral bodies. In the deployed, impaction position, the blade region of the blades extends generally superiorly or inferiorly beyond the superior and inferior surfaces of the implant and into the adjacent superior and inferior vertebral bodies to prevent the implant from moving out of position over time. When the blades are deployed, the implant resists left to right rotation and resists flexion and/or extension. Additionally, the fixation elements are locked in place to prevent accidental removal from the implant. Following insertion in a disc space, the implant is contained within the excised disc space and does not protrude past the anterior wall of the vertebral body. Thus, the system has a zero anterior profile. Additionally, preparations of the anterior surface of the adjacent vertebral body/bodies are minimized because the implant does not lie against this surface.

The implant is pre-assembled with the fixation system. In the insertion position, as shown in FIGS. 1A-1D, 5A, 5B, and 10B, the strike plates extend beyond the anterior side and the blades (including the blade region) are completely inside the implant.

1. Blades

The implant contains one or more fixation elements to resist left to right rotation and to resist flexion and/or extension of the implant. Typically the fixation elements are blades.

The fixation system includes one or more blades (107a, 107b, 307a) as illustrated in FIGS. 3, 12A-12D, 13A-13E and 14A-14F. The blades include a blade region (122a, 122b, 322a, 322b) and a support region (120a, 120b, 320a, 320b).

a. Support Region

The support region has an outer surface (145a), an inner surface (146a) and two ends (148a, 148b), each of which have a protrusion that contacts a corresponding depression or track in an interior surface of the implant body. The protrusion functions as a joint to join two or more different elements in an implant together while allowing motion between the elements.

i. End Protrusions

As shown in the Figures, the protrusion at each end (148a, 148b) of the support region may be a dovetail protrusion (102a-102d) (also referred to herein as a "dovetail") that extends from the end of the support region and joins with an interior surface of a side wall of the body and allows the blade to move inferiorly or superiorly from a first, insertion position to second impaction position. The dovetail protrusion, as shown in the Figures typically has angled sides. Optionally the blade can move from an impaction position to the first (insertion position), to allow for removal of the implant, if needed. In the insertion position (shown in FIGS. 1A-1D, 5A, 5B, 10B), the blades, including the blade regions thereof, are located and contained inside the implant and are positioned such that the blade region of a first blade is directed superiorly and the blade region of the second blade is directed inferiorly.

The implant is inserted into the vertebral body in the insertion position. The blades are connected to the implant via their protrusions, which fit into the tracks located on interior surfaces of the implant. The protrusions on the ends of the support region of the blades are in sliding relation to the tracks, allowing the blades to slide anteriorly or superiorly inside the implant.

One skilled in the art would understand that the end protrusions can adopt many different shapes as long as the shape is complementary to the tracks on an interior surface of the implant. The cross-sectional shape may be a symmetric shape or a non-symmetric shape. Exemplary cross-sectional shapes include but are not limited to T-shapes, C-shapes, I-shapes, dovetailed shapes with angled sides, any portion of a circle, a triangle, an ellipse, a polygon, a star, a square, a rectangle, an oval, a hexagon, or an octagon. The corresponding tracks located on the interior surfaces of each implant have a shape that corresponds with the shape of the cross-section of the protrusion and maintains the protrusion in the track, while allowing it to slide along the track.

Figures 12A, 12B:
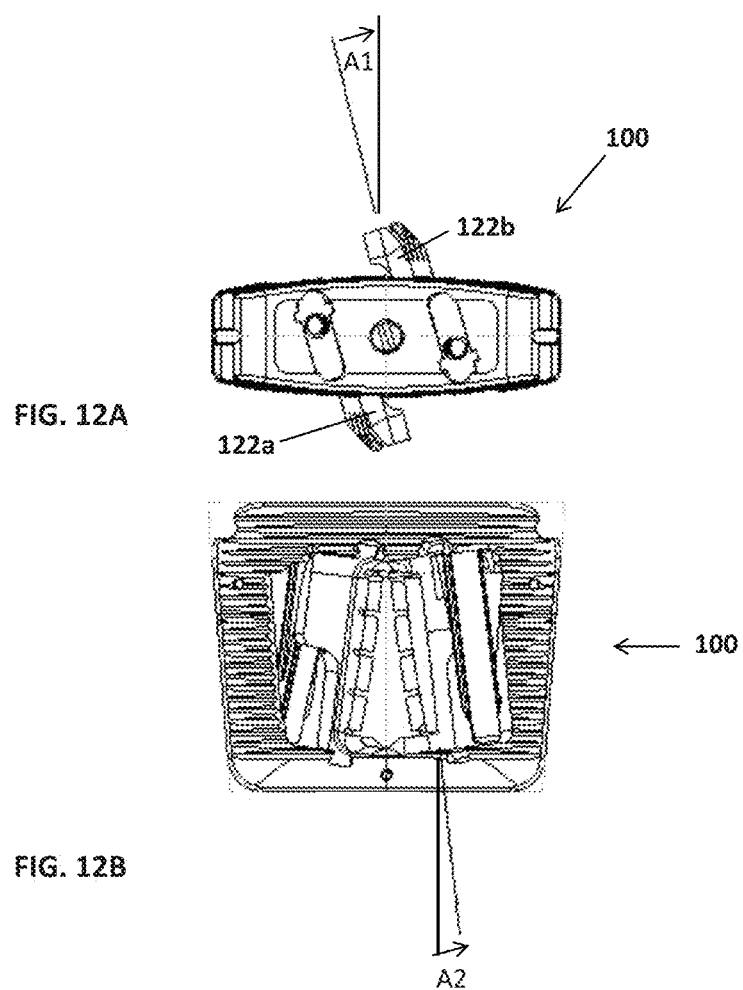
FIGS. 12A and 12B show elevation and plan views of the implant depicted in FIGS. 1A-1D, with the angle of the blade labeled.

When sliding, the blades typically move generally vertically or at a compound angle, defined by a first angle in a first plane and a second angle in a second plane, relative to the body of the implant. For example, as shown in FIGS. 12A and 12B, angle A1 can range from 10° to 20° or any angle there between, such as 11°, 12°, 13°, 14°, 15°, 16°, 17°, 18°, 19°, or 20°. In a preferred embodiment, the A1 angle is 15°. Angle A2 can range from 5° to 15° or any angle there between, such as 5°, 6°, 7°, 8°, 9°, 10°, 11°, 12°, 13°, 14°, or 15°. In a preferred embodiment, the A2 angle is 7°. Optionally, the angle is not a compound angle and A2 is 0°.

The blades are sufficiently strong such that they do not deform when moved from the insertion position to the impaction position.

b. Attachment Region(s)

The support region of the blades also contains one or more attachment regions (149a, 349a) configured to attach to one or more strike plates in a manner that keeps the strike plates and blades aligned as the strike plate moves in a longitudinal manner from a first position to a second position.

i. Attachment Region Track

The attachment region (149a, 349a) typically includes an attachment region track (114) defined by a ramp (115) and two side walls (124a, 124b). The opening between the side walls and the ramp defines a channel (189, 389).

The ramp (115) is configured to allow the hypotenuse surface (132) of the strike plate (108a, 108b) (see FIGS. 9A, 9B, and 14B) to slide along its angled surface when the strike plate moves from a first, insertion position to a second, impaction position. The back portion of the ramp (115) may connect with a substantially horizontal surface (113) (see FIGS. 13F and 13G).

The blades are oriented in the implant body such that the angled ramps of the blades slope in opposite directions. For example, in an ALIF implant, the blades are positioned inside the implant body such that the tracks in the support region are proximal to the anterior side of the implant.

In some embodiments, the strike plates contain a protrusion on their hypotenuse surface that mates with a correspondingly shaped ramp in the support portion of the blade. For example, the ramp can be in the shape of a T-shaped track (382a), which is configured to engage a T-shaped protrusion (380a) of the hypotenuse surface (332) of the strike plate (308a) (see FIGS. 14A-F). In this embodiment, the T-shaped track contains an upper surface (386), two interior side wall surfaces (387a, 387b), two lower side wall protrusions (388a, 388b), and a channel defined by the upper surface, interior side wall surfaces and lower side wall protrusions (389) (see FIGS. 14D and 14F).

Figure 13A:
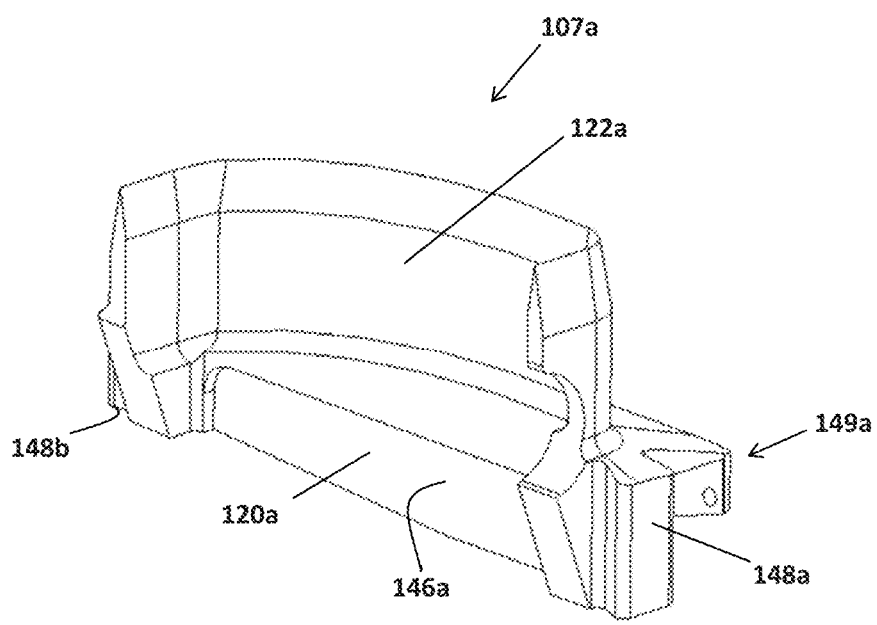
FIGS. 13A-13G show various views of an exemplary blade.
Figure 13B:
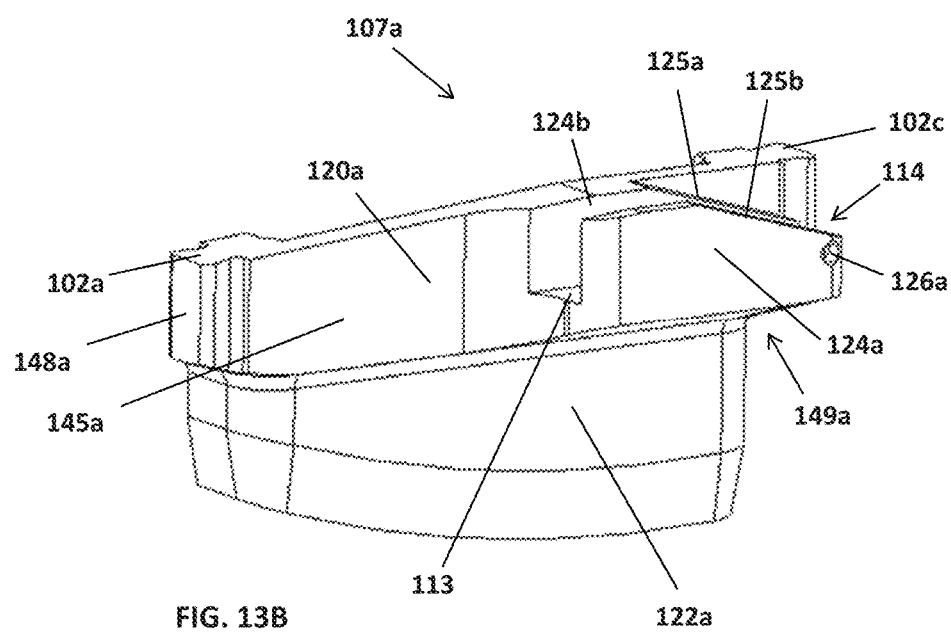
Figure 13C:
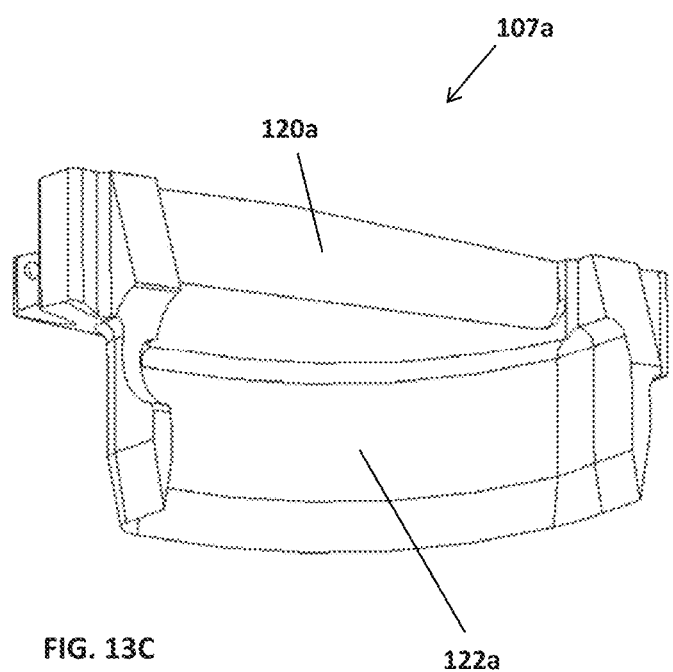
Figure 13D:
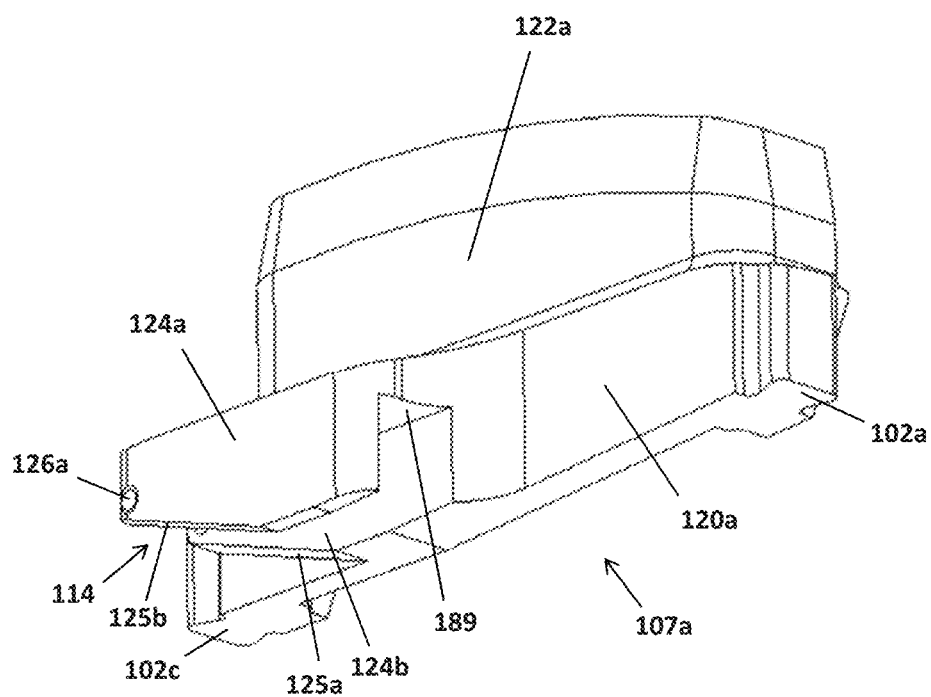
Figure 13E:
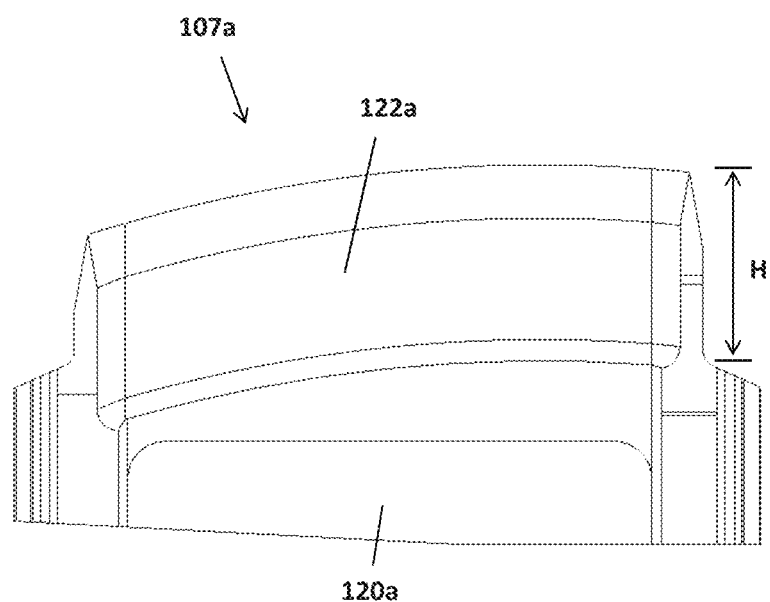
Figure 13F:
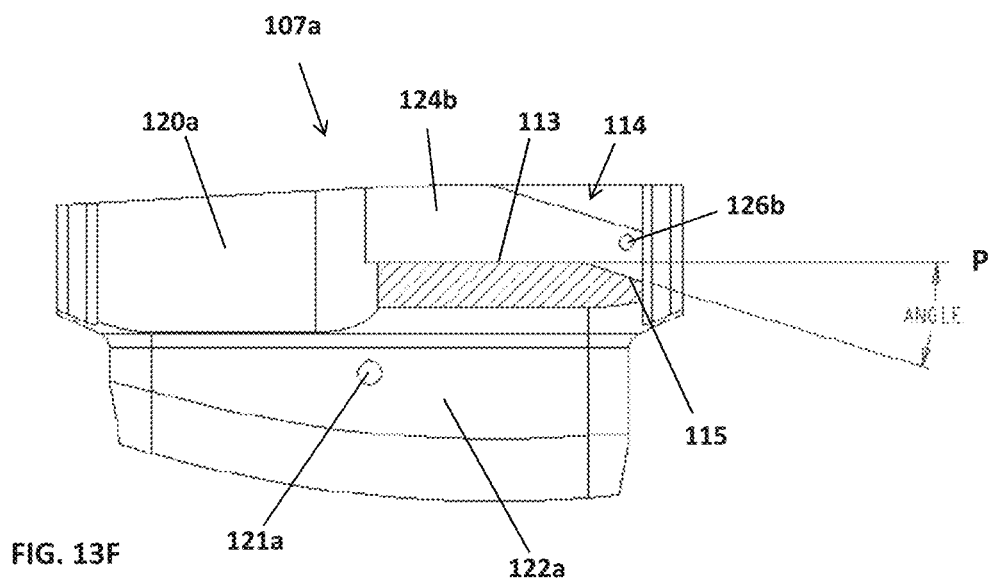
Figure 13G:
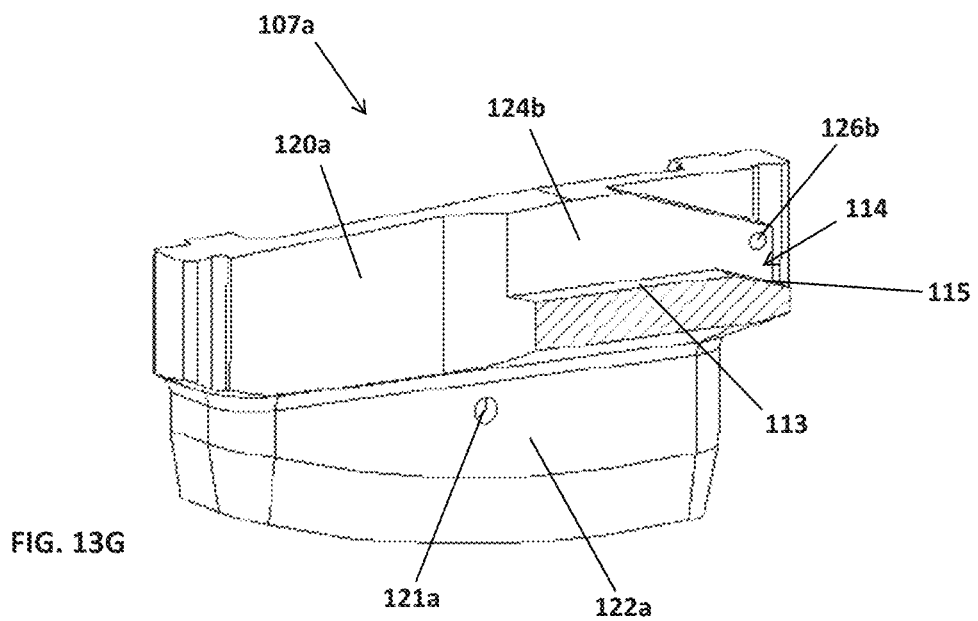
Figure 14A:
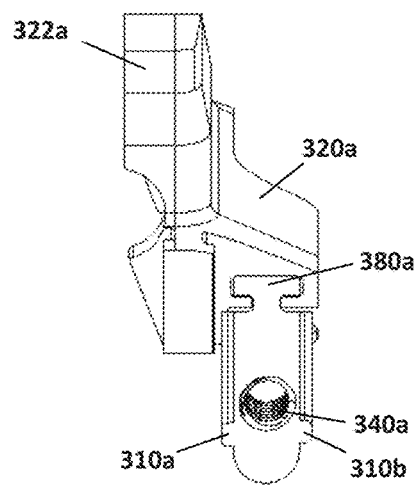
FIGS. 14A-14C show various views of a strike plate attached to a blade. In these Figures, the T-shaped protrusion of the strike plate fits into a correspondingly shaped T-shaped track in the support region of the blade.
Figure 14B:
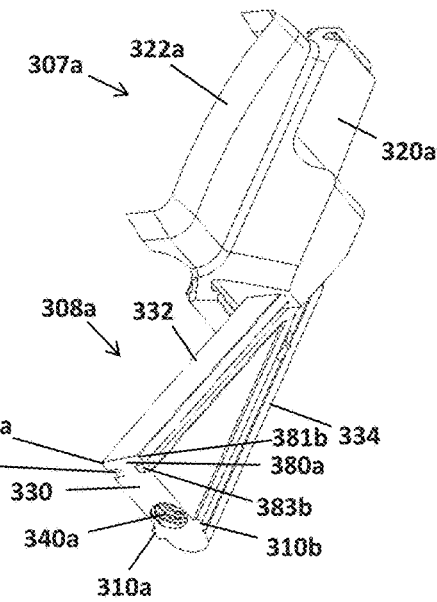
Figure 14C:
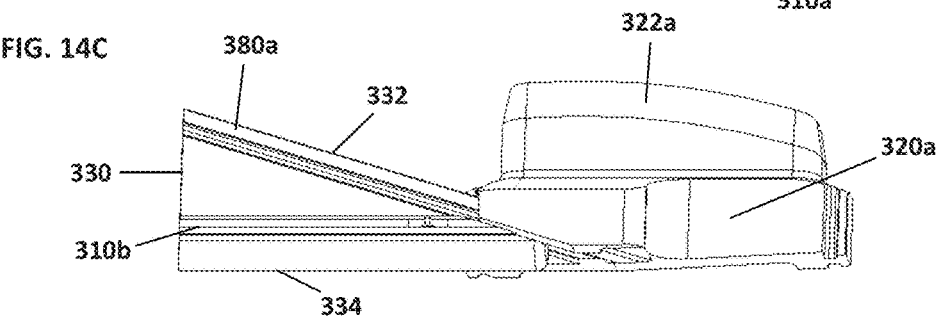

In some embodiments, the angle of the ramp (115) ranges from 20° to 35°, optionally from 21° to 33°, or any angle or range of angles there between, measured from the plane (P) (as identified on FIG. 13F). The angle for the ramp varies depending on the size of the implant. For example, for implants with a height (h) of 11 mm, preferably, the angle of the ramp is 21°. For implants with a height (h) of 13 mm, preferably, the angle of the ramp is 24°. For implants with a height (h) of 15 mm, preferably, the angle of the ramp is 26°.

Preferably the upper surface (125a) of the side wall (124a) slopes at the same angle as the angle of the ramp. This allows the strike plate to apply a force against the surface as it pushes the blade into the impaction position. Similarly, utilizing the same angle on the upper surface as in the ramp may facilitate removal of the blade, such as in a revision procedure or during initial placement of the implant in a patient. In these methods, the strike plates are pulled out of the impaction position and return to an insertion position, thereby removing the blades from the adjacent vertebral bodies.

c. Pin

Figure 5A:
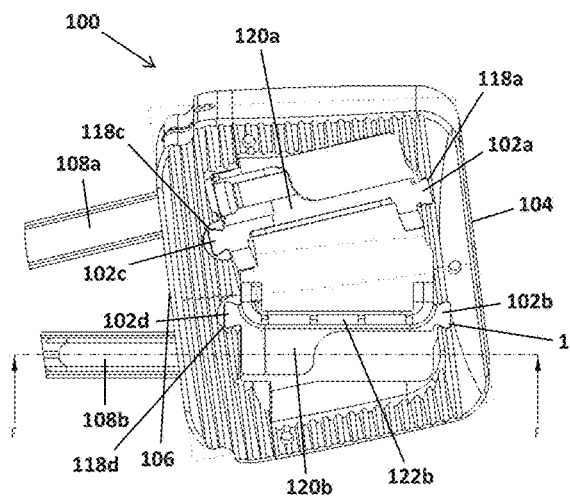
FIGS. 5A and 5B show perspective and cross-sectional perspective views, respectively, of the implant depicted in FIGS. 1A-1D in the insertion position, with the strike plates protruding from the anterior side of the implant.
Figure 5B:
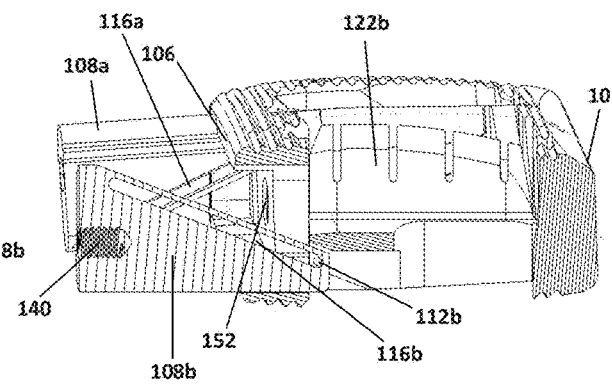

In some embodiments, the attachment region includes a pin to attach the strike plate and maintain it inside the track. For example, the attachment region may contain a cylindrical pin (112a or 112b), which is attached to the side walls, such as by fitting in circular depressions (126a, 126b). In these embodiments, the pin fits in and slides along an axial slot that runs generally parallel to the hypotenuse surface of the strike plate (see, e.g. the pin (112b) in the slot (116b) as depicted in FIGS. 4B and 5B).

Preferably, the side walls contain circular depressions (126a, 126b) proximal to the end of the ramp that is closest to the anterior side of the implant. In these embodiments, each of these depressions is configured to receive a pin (112a, 112b). In this embodiment, the strike plates can be attached to the support regions of the blades via a pin that slides through a slot in that runs parallel to the hypotenuse surface of a strike plate.

i. Track that Mates with Shape of the Strike Plate Protrusion

In other embodiments, the attachment region does not include a pin, rather the track has a shape that corresponds with and mates with the shape of a protrusion (which terminates on one side with the hypotenuse surface) on the strike plate (referred to herein as a "strike plate protrusion"). In these embodiments, the attachment region connects the support region of the blade to a strike plate via the axial track. For example, each of the side walls (124a, 124b) may contain a side wall protrusion (388a, 388b) that extends substantially perpendicular to the interior surface of the side wall (387a, 387b) and mates with a corresponding depression in the strike plate protrusion to retain the strike plate within the track.

For example, if the strike plate protrusion is in the shape of a dovetail, the channel of the track in the attachment region defines a similarly shaped dovetail cross-section, i.e. a dovetail track. Alternatively, if the strike plate protrusion is in the shape of a "T", such as depicted in FIGS. 14A-14F, the attachment region contains a channel with a similarly shaped T-shaped cross-section, i.e. a T-shaped track.

It is understood that alternative shapes for the channel in the track of the attachment region (and the corresponding protrusion on the strike plate) may be used as long as these shapes are complementary and allow the hypotenuse surface of the strike plate to slide along the track while remaining inside the track. The cross-sectional shape of the channel may be a symmetric shape or a non-symmetric shape. Exemplary cross-sectional shapes include but are not limited to T-shapes, C-shapes, !-shapes, dovetailed shapes with angled sides, any portion of a circle, a triangle, an ellipse, a polygon, a star, a square, a rectangle, an oval, a hexagon, or an octagon.

d. Blade Region

The blade region of an exemplary blade is shown in FIGS. 13A-13G. The height of the blade region is designated with H. In some embodiments, the height (H) of the blade region ranges from 3 mm to 9 mm. Preferably, the height of the blade region (H) is 5.75 mm. In other embodiments, such as the lateral LIF embodiment(s), the blade height can range from 3 mm to 18 mm.

When the implant is in the impaction positions, the length of engagement of the blade region in the adjacent vertebral body typically ranges from about 2.5 mm to 8.5 mm.

When the implant is in the impaction position and the blades are deployed, typically the total height of the implant from the tip of one blade to the tip of the other blade (including the deployed blades) increases by about 100 to 250% compared to the height of the implant in the insertion position.

As depicted in the Figures, in some embodiments the blade region (122a, 122b, 322a, 322b) of the blade has multiple projections that are separated by spaces. In other embodiments the blade region of the blade can also be a continuous surface.

Optionally, the blade region also has a marker that is visible by s suitable diagnostic method, such as x-ray. Suitable markers include a hole (121a) in any shape (e.g. circle or other shapes) or a marker formed from a material that is different than the material on the blade, which allows the practitioner to see when the blade is fully deployed when viewed on an X-Ray (see FIGS. 13F and 13G).

2. Strike Plates

In one embodiment, the strike plates (108a, 108b, 308a, 308b) are shaped like a right-angled wedge, formed of two surfaces (130, 134, 330, 334) adjacent to the right angle, and a hypotenuse surface (132, 332) opposite the right angle (as shown in FIGS. 9A, 9B, 14B, 14C, and 14E). The hypotenuse surface of each of the right-angled wedges fits into an angled ramp (114) that is located on the support region of the blade, in sliding relation thereto. The hypotenuse surface of the strike plate slides along the angled bottom surface of the ramp (FIG. 3).

In the insertion position, the strike plates (108a, 108b, 308a, 308b) protrude from one side of the exterior surface (131) of the implant. For example, for an ALIF implant, the strike plates protrude from the anterior side (106) of the implant (as seen in FIGS. 1A-1D, 5A, and 5B). For a LIF, the strike plates protrude from a lateral side of the implant. The strike plates are arranged in the implant such that the hypotenuse surfaces of the strike plates slope in opposite directions. The right angle of one strike plate is adjacent to the superior surface of the implant, and the right angle of the other strike plate is adjacent to the inferior surface of the implant. In this position the blades are contained inside the implant. The blades are positioned inside the implant such that when the strike plates are pushed into the implant, the hypotenuse surfaces of the strike plates slide along the ramps and push the blades inferiorly or superiorly inside the implant. In the resulting impaction position, at least some of each blade region is superior or inferior to the superior or inferior surface of the implant (as shown in FIGS. 2B-2D, 4B, 7A, 8A, 8B, and 10A).

Optionally, each strike plate also has bilateral retention rails (110a-110d, 310a, 310b), with one retention rail on each side of each strike plate. Each of the bilateral retention rails aligns with and fits inside a corresponding depression (154a-154d) on the anterior side (155) of the implant (see, e.g. FIG. 8B). These rails secure the strike plates to the implant when they are fully extended beyond the anterior side (106) of the implant, such as when they are in the insertion position.

Additionally, each strike plate may contain an insertion region, such as an indent, depression, or a threaded hole (140a, 140b, 340a, 340b) to mate with a portion of an insertion device, to facilitate movement of the strike plates from the insertion position to the impaction position.

Figure 9A:
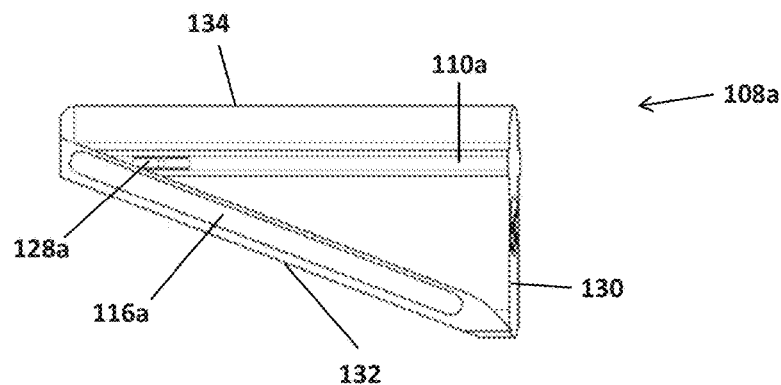
FIGS. 9A and 9B show a side view and perspective view, respectively, of an exemplary strike plate used in the implant depicted in FIGS. 1A-1D.
Figure 9B:
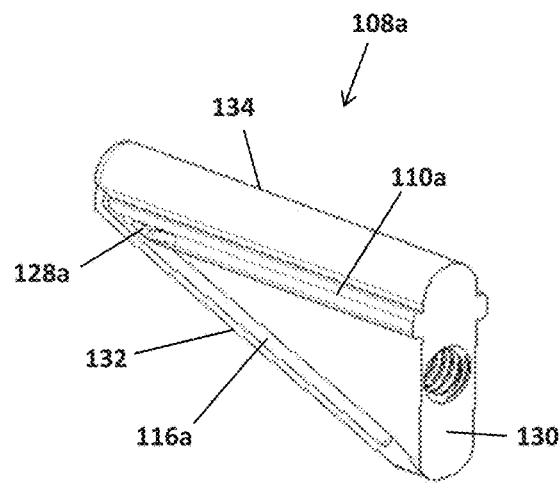

While the implant is loaded into an insertion device, the strike plates are prevented from being pushed into the implant by retention bumps (128a, 128b) present on the outer retention rail of each strike plate (FIGS. 9A and 9B).

A retention bump is preferably located at the posterior end of each strike plate. Typically each strike plate contains one retention bump on one side, typically the outward facing retention rail (110a and 110d; 310a and 310d), at the posterior end. In the insertion position, the retention bumps extend just beyond and are adjacent to a depression (154a and 154d) on the anterior side (155) of the implant. This prevents accidental deployment of the blades and damage of interior structures in the patient.

The retention bumps are small and protrude from the retention rail. In some embodiments this protrusion ranges from 0.1 mm to 0.4 mm, preferably 0.1 to 0.3 mm, and more preferably 0.24 mm. The resistance of the retention bumps against the anterior side can be overcome and the strike plates can be pushed into the implant and along the adjacent depression by applying a small force.

a. Slot

In one embodiment, each strike plate also contains an open slot (116a, 116b) that runs parallel to the hypotenuse surface of the wedge. Each strike plate is secured to a blade by a pin (112a, 112b) that fits through a first hole or depression (126a) in the first side wall (124a) of the angled ramp of the blade, through the open slot (116a, 116b) of the strike plate, and through a second hole or depression (126b) of the second angled side wall (124b) of the angled ramp of the blade.

b. Strike Plate Protrusion

In some embodiments, the hypotenuse surface of each strike plate is part of a protrusion (referred to herein as a "strike plate protrusion") that fits inside a correspondingly shaped attachment region track in the support region of the blade. For example, the strike plate protrusion can be in the shape of a T-shaped protrusion (380a) that fits into a T-shaped attachment region track (382a) (see FIGS. 14A-14F). In this embodiment the T-shaped protrusion has an upper hypotenuse surface (332), two outer lateral surfaces (381a, 381b), and a depression (383a, 383b) beneath each of the lateral surfaces, which defines a protrusion having a cross-section in the shape of a "T" (see FIGS. 14B and 14E).

One skilled in the art would understand that the strike plate protrusion can adopt many different shapes as long as the cross-section of the protrusion is complementary in shape to the cross section of the attachment region track. The strike plate protrusion of the track may be a symmetric shape or a non-symmetric shape. Exemplary cross-sectional shapes include but are not limited to T-shapes, C-shapes, I-shapes, dovetailed shapes with angled sides, any portion of a circle, a triangle, an ellipse, a polygon, a star, a square, a rectangle, an oval, a hexagon, or an octagon.

3. Additional Components a. Cover Plate

Figure 11A:
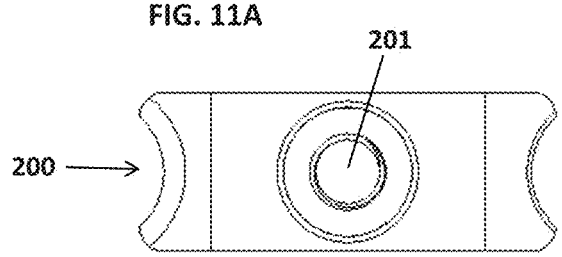
FIGS. 11A and 11B show elevation and side views (respectively) of an exemplary cover plate that is attachable to the implant depicted in FIGS. 1A-1D.
Figure 11B:
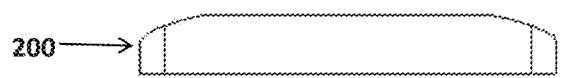
Figure 11C:
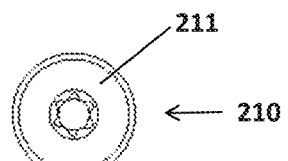
FIGS. 11C and 11D show elevation and side views (respectively) of an exemplary screw that can be used to secure the cover plate to the outer surface of the implant body after insertion.
Figure 11D:
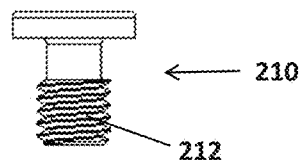

Following insertion of the implant into the spine and impaction of the blades, a front cover plate (200) (FIGS. 11A and 11B) is typically added to prevent the one or more strike plates from backing out. The cover plate contains a central hole (201), which aligns with the screw hole (152) on a side (e.g., for an ALIF, the anterior side and for a lateral LIF, a lateral side) of the implant. A screw (210) is threaded through the central hole (201) and the screw hole (152) to secure the cover plate to the implant.

In a preferred embodiment, the process is reversible, allowing one to remove the implant, by first removing the cover plate. With the cover plate removed, each of the strike plates is accessible and can be engaged at the threaded connection (140, see FIGS. 4B and 5B) and attached to an insertion tool. The insertion tool can pull the strike plates back to the original insertion position, which pulls the blades out of the adjacent superior and inferior vertebral bodies. In this position, which corresponds with the insertion position, the blades, including the blade region, are inside the implant. This allows for the removal of the implant without destroying the implant, if necessary, such as in a revision procedure.

b. Insertion Tool

An implant insertion tool is used to insert the implant described herein into the desired location in the spine. The implant insertion tool contains threaded screws and/or gripping arms to connect with the insertion side of the implant. Additionally, typically the insertion tool contains threaded screws positioned and sized to fit in the corresponding threaded connections (140) in the strike plates to push the strike plates into the impaction position. However, alternative elements may be present on the insertion tool to connect it with the implant.

III. Kit

The implant may be provided as part of a kit for an ALIF or a LIF. The kit may contain at least one intervertebral implant as described above, and a cover plate. The kit may also contain an insertion tool. The kit also typically contains instructions for care and insertion of the spinal fixation system. In some embodiments, more than one implant is provided in the kit. Preferably, the kit contains a plurality of different sized implants to allow for use with patients with different anatomies.

It may not be clear what size implant is needed until the surgery has begun. Having a kit that provides several options allows for the appropriately sized implant to be selected based on the patient's anatomy. The kit may provide one or more different intervertebral implants, optionally different sized implants, and optionally more than one different sized and/or shaped blades.

In some embodiments the size of the implant is 23 mm×28 mm. In some embodiments, the size of the implant is 26 mm×32 mm. In other embodiments, the size of the implant is 32 mm×38 mm. In some embodiments, the lordosis of the implant is 8°. In other embodiments, the lordosis is 15°. In some embodiments, the implant is 11 mm, 13 mm, 15 mm, 17 mm, 19 mm, or 21 mm high, or any height in between these listed values. An exemplary implant (100) suitable for an anterior approach is illustrated in FIGS. 1A-8B.

The kit may also include tool(s) for placement of the implant and fixation system. In one embodiment, the kit can include tools and materials for inserting bone graft material. For example, the kit can include a syringe or other apparatus for injecting bone graft material.

IV. Methods of Use

A. Preparation of Patient

The intervertebral disc is removed, and the disc space is prepared as usual prior to insertion of the implant. Typically the adjacent inferior and superior endplates are roughened.

B. Implant Sizing and Selection

When selecting an implant, the height, profile, and footprint of the intervertebral space is typically evaluated. One or more trial implants may be inserted into the disc space to find the correct size. Trial implants have the same dimensions as the permanent implants and can be used to visualize the implant positioned in the disc space. Different sized and shaped trial implants are inserted into the disc space until the trial implant with the best contact between both the inferior and superior endplates is found. A mallet or tuning fork can be used to insert and remove the trial implant. Fluoroscopy can be used for visualization.

C. Implant Preparation

Following implant selection, the selected implant is typically loaded with bone graft or bone graft substitute material. For example, as shown in FIG. 1A, bone graft material can be inserted in the opening (160) between the two blades and/or in each or both of the openings (162a and 162b) between the opposite side of each blade and adjacent wall, i.e. a lateral side portion, of the implant. In a preferred embodiment, a volume of bone graft can be loaded into the implant in a range of 2.88 cc to 8 cc, optionally, even greater amounts of bone graft material may be loaded in the implant, such as from about 6 to 20 cc.

In some embodiments, the implant is loaded onto an insertion tool prior to insertion into the spine. While the implant is loaded on the insertion tool, the one or more strike plates are prevented from being deployed due to retention bumps (128a, 128b) located on the exterior retention rail of each strike plate (FIGS. 3, 9A, and 9B), which are in contact with an exterior surface (131) of the implant body (e.g. for an ALIF, this exterior surface is located on the anterior side of the implant body) and protrude slightly beyond the adjacent depression (154a and 154d).

D. Implant Insertion

The implant is inserted into the prepared disc space. If necessary, a mallet can be used to advance the implant into the desired position in the intervertebral disc space. The strike plates are pushed, typically using an insertion tool, until they are fully inside the implant, and in turn, the strike plates deploy the blades, so that the blades are inserted into the inferior and superior vertebral bodies. Preferably, the process of impaction is monitored using fluoroscopy. Finally, a cover plate may be placed over the anterior side of the implant to prevent the strike plates from backing out of the implant. A screw (210) or any alternative fixation device may be placed in the cover plate (200) to secure the plate to the implant. Optionally, the screw is affixed to the cover plate prior to placement of the cover plate on the anterior side of the implant.

E. Optional Reversion

If necessary, following insertion, the implant may be removed from its position in the spine. First, the cover plate (200) is removed by unscrewing the cover plate from the screw hole (152) on the anterior side of the implant. A connection on an inserter is threaded into the threaded holes (140a, 140b) of the one or more strike plates, allowing the one or more strike plates to be pulled out into the insertion position.

The resulting retraction of the blades into the body of the implant allows the practitioner to pull the implant out of, or adjust its position between the adjacent vertebral bodies without destroying the implant.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An implant comprising a body and a bone fixation system,
the body including an interior area disposed between a superior surface and an opposite inferior surface;
the bone fixation system comprising at least one blade disposed within the interior area of the body in an insertion position, the at least one blade including a blade region and a support region;
the bone fixation system further including at least one strike plate comprising a sloped surface;
the support region of the at least one blade comprising an attachment region attaching the at least one blade to the at least one strike plate;
wherein the attachment region includes a ramp; and
wherein the sloped surface of the at least one strike plate is configured to slide along the ramp to move the at least one blade from the insertion position to an impaction position, wherein at least a portion of the blade region of the at least one blade protrudes past one of the superior surface and inferior surface of the body in the impaction position; and
wherein the blade region of the blade includes a first free end defined by a first lateral edge and a second free end defined by a second lateral edge, the second free end disposed substantially opposite the first lateral edge.

2. The implant according to claim 1, wherein the sloped surface of the at least one strike plate includes a strike plate protrusion that fits inside a correspondingly shaped track in the attachment region of the at least one blade.

3. The implant according to claim 1, wherein the at least one blade comprises a first blade and a second blade.

4. The implant according to claim 3, wherein at least a portion of the blade region of the second blade protrudes past the inferior surface of the body in the impaction position.

5. The implant according to claim 1, wherein the blade region of the first blade is configured to extend back into the interior area of the body when the first strike plate is pulled outwards from the body of the implant.

6. An implant comprising:
a body; and
a bone fixation system;
the body including an interior area disposed between a superior surface and an opposite inferior surface spaced from the superior surface in a vertical direction;
the bone fixation system including at least one blade disposed within the interior area of the body in an insertion position;
the bone fixation system further including at least one strike plate engaging the at least one blade in the interior area of the body, the at least one strike plate being configured to move the at least one blade from the insertion position to an impaction position in which at least a portion of the blade protrudes past one of the superior surface and inferior surface of the body; and
the at least one blade including a first blade, wherein movement of the first blade from the insertion position to the impaction position is in a direction at a first non-zero angle with respect to the vertical direction;
wherein the first blade is disposed on a first side of a lateral centerline of the body and deploys, at the first non-zero angle, toward a vertical plane extending through the lateral centerline of the body.

7. The implant of claim 6, wherein the first non-zero angle is in the range of 10-20 degrees.

8. The implant of claim 7, wherein the first non-zero angle is approximately 15 degrees.

9. The implant of claim 8, wherein the at least one blade further includes a second blade;
wherein movement of the second blade from the insertion position to the impaction position is in a direction at a second non-zero angle with respect to the vertical direction; and
wherein the second blade is disposed on a second side of the lateral centerline of the body and deploys, at the second non-zero angle, toward the vertical plane extending through the lateral centerline of the body.

10. The implant of claim 9, wherein the first blade has a first distal end and the second blade has a second distal end; and
wherein, when the first blade and the second blade are disposed in the impaction position, the first distal end of the first blade and the second distal end of the second blade are disposed approximately in the vertical plane extending through the lateral centerline of the body.

11. The implant of claim 9, wherein the second blade is oriented, in a horizontal plane, at a second non-zero horizontal angle with respect to an anterior-posterior axis of the body.

12. The implant of claim 6, wherein the first blade is oriented, in a horizontal plane, at a first non-zero horizontal angle with respect to an anterior-posterior axis of the body.

13. The implant of claim 12, wherein the first non-zero horizontal angle is in the range of 5-15 degrees.

14. The implant of claim 13, wherein the first non-zero horizontal angle is approximately 7 degrees.

15. An implant comprising:
a body; and
a bone fixation system;
the body including an interior area disposed between a superior surface and an opposite inferior surface spaced from the superior surface in a vertical direction;
the bone fixation system including a first blade disposed within the interior area of the body in an insertion position;
the bone fixation system further including at least one strike plate engaging the first blade in the interior area of the body, the at least one strike plate being configured to move the first blade from its insertion position to an impaction position in which at least a portion of the first blade protrudes past the superior surface; and
the first blade including a first wall and a second wall extending substantially parallel to one another and a third wall longer than the first wall and the second wall and extending between the first wall and the second wall such that the arrangement of the first wall, second wall, and third wall has a U-shaped cross-section in a plane that is substantially perpendicular to the direction in which the first blade is configured to move;
wherein the third wall of the first blade defines a first plane that is oriented at a first non-zero, oblique, horizontal angle with respect to an anterior-posterior axis of the body.

16. The implant of claim 15, wherein the first non-zero horizontal angle is in the range of 5-15 degrees.

17. The implant of claim 16, wherein the first non-zero horizontal angle is approximately 7 degrees.

18. The implant of claim 15, further including:
a second blade disposed within the interior area of the body in an insertion position;
the second blade being deployable from its insertion position to an impaction position in which at least a portion of the second blade protrudes past the inferior surface; and
the second blade including a first wall and a second wall extending substantially parallel to one another and a third wall longer than the first wall and the second wall and extending between the first wall and the second wall such that the arrangement of the first wall, second wall, and third wall has a U-shaped cross-section in a plane that is substantially perpendicular to the direction in which the second blade is configured to move;
wherein the third wall of the second blade defines a second plane that is oriented at a second non-zero horizontal angle with respect to the anterior-posterior axis of the body; and
wherein the first non-zero horizontal angle and the second non-zero horizontal angle are substantially the same.

19. The implant of claim 15, the bone fixation system further including a second blade disposed within the interior area of the body in an insertion position;
the second blade including a fourth wall and a fifth wall extending substantially parallel to one another and a sixth wall longer than the fourth wall and the fifth wall and extending between the fourth wall and the fifth wall such that the arrangement of the fourth wall, fifth wall, and sixth wall has a U-shaped cross-section in a plane that is substantially perpendicular to the direction in which the second blade is configured to move;
wherein the first plane containing the third wall of the first blade is oriented at an oblique angle with respect to a second plane containing the sixth wall of the second blade.

* * * * *